(12) United States Patent
Kuperman et al.

(10) Patent No.: US 6,362,349 B1
(45) Date of Patent: Mar. 26, 2002

(54) PROCESS FOR THE DIRECT OXIDATION OF OLEFINS TO OLEFIN OXIDES

(75) Inventors: Alex Kuperman; Robert G. Bowman; Howard W. Clark; George E. Hartwell, all of Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/647,771

(22) PCT Filed: Apr. 7, 1999

(86) PCT No.: PCT/US99/07714

§ 371 Date: Oct. 4, 2000

§ 102(e) Date: Oct. 4, 2000

(87) PCT Pub. No.: WO99/52883

PCT Pub. Date: Oct. 21, 1999

Related U.S. Application Data

(60) Provisional application No. 60/081,826, filed on Apr. 15, 1998.

(51) Int. Cl.[7] ................. C07D 301/06; C07D 301/08
(52) U.S. Cl. ................. 549/533; 549/532; 549/536; 549/537
(58) Field of Search ................. 549/533, 532, 549/536, 537

(56) References Cited

U.S. PATENT DOCUMENTS

| | | | |
|---|---|---|---|
| 2,974,161 A | 3/1961 | Keith et al. | 260/491 |
| 3,316,279 A | 4/1967 | Fenton | 260/348.5 |
| 3,641,066 A | 2/1972 | Rouchaud et al. | 260/348.5 |
| 3,717,662 A | 2/1973 | Alagy et al. | 260/348.5 |
| 3,888,889 A | 6/1975 | Kolombos et al. | 260/348.5 |
| 3,957,690 A | 5/1976 | Bobolev et al. | 252/462 |
| 3,963,645 A | 6/1976 | Gelbein | 502/248 |
| 4,007,135 A | 2/1977 | Hayden et al. | 252/467 |
| 4,740,487 A | 4/1988 | Matheson et al. | 502/66 |
| 4,864,041 A | 9/1989 | Hill | 549/513 |
| 5,008,414 A | 4/1991 | Ramachandran et al. | 549/538 |
| 5,120,866 A | 6/1992 | Castellan et al. | 549/523 |
| 5,407,888 A | 4/1995 | Herzog et al. | 502/317 |
| 5,447,897 A | 9/1995 | Kemp | 502/303 |
| 5,525,741 A | 6/1996 | Sugita et al. | 549/536 |

FOREIGN PATENT DOCUMENTS

| | | |
|---|---|---|
| EP | 0 709 360 A1 | 5/1996 |
| WO | 95/01837 | 1/1995 |
| WO | 96/02323 A1 | 2/1996 |
| WO | 97/25143 | 7/1997 |
| WO | 97/34692 | 9/1997 |
| WO | 97/47386 | 12/1997 |
| WO | 98/00414 | 1/1998 |
| WO | 99/00188 | 1/1999 |
| WO | 00/59632 | 10/2000 |
| WO | 00/59633 | 10/2000 |

OTHER PUBLICATIONS

Derwent 68/21190R, Sep. 1968.
Derwent 85–000456/01, Jan. 1983.
Derwent 85–000502/01, Jan. 1983.
Derwent 85–012848/03, May 1983.
Derwent 96–333814/33, Dec. 1994.
Mark Ward et al., "Epoxidation of Propylene Over Molybdenum–Y Zeolites," *Journal of Molecular Catalysis*, 27 (1984), 1–10.
K. Weissermel and H. J. Arpe, *Industrial Organic Chemistry*, 2nd edition, VCH Verlagsgesellschaft mbH, Weinheim, Germany, 1993, pp. 141–146 and pp. 264–269.

*Primary Examiner*—Ba K. Trinh
(74) *Attorney, Agent, or Firm*—Marie F. Zuckerman

(57) ABSTRACT

A process for the direct oxidation of an olefin by oxygen to the corresponding olefin oxide in the presence of a reducing agent and a catalyst. The catalyst comprises a metal component, such as a transition metal oxide, dispersed on a metal ion-exchanged metallosilicates, such as a Group 1 or Group 2 ion-exchanged porous aluminosilicate. Selectivity to the olefin oxide is high and the catalyst is readily regenerated.

30 Claims, No Drawings

PROCESS FOR THE DIRECT OXIDATION OF OLEFINS TO OLEFIN OXIDES

This application is a 371 of PCT/US 99/07714 filed on Apr. 7, 1999 which claims benefit of provisional application No. 60/081,826 dated Apr. 15, 1998.

This invention was made with United States Government support under Cooperative Agreement No. 70NANB5H1143 awarded by NIST. The United States Government has certain rights in the invention.

This invention pertains to a process for the direct oxidation of olefins, such as ethylene and propylene, by oxygen to olefin oxides, such as ethylene oxide and propylene oxide.

Olefin oxides, such as propylene oxide, are used to alkoxylate alcohols to form polyether polyols, such as polypropylene polyether polyols, which find significant utility in the manufacture of polyurethanes and synthetic elastomers. Olefin oxides are also important intermediates in the manufacture of alkylene glycols, such as propylene glycol and dipropylene glycol, and alkanolamines, such as isopropanolamine, which are useful as solvents and surfactants.

Propylene oxide is produced commercially via the well-known chlorohydrin process wherein propylene is reacted with an aqueous solution of chlorine to produce a mixture of propylene chlorohydrins. The chlorohydrins are dehydrochlorinated with an excess of alkali to produce propylene oxide. This process suffers from the production of a low concentration salt stream. (See K. Weissermel and H. J. Arpe, *Industrial Organic Chemistry*, $2^{nd}$ ed., VCH Publishers, Inc., New York, N.Y., 1993, pp. 141–146 and 264–265.)

Another commercial route to propylene oxide relies on the transfer of an oxygen atom from an organic hydroperoxide or peroxycarboxylic acid to an olefin. In the first step of this process, a peroxide generator, such as isobutane or acetaldehyde, is autoxidized with oxygen to form a peroxy compound, such as t-butyl hydroperoxide or peracetic acid. This compound is used to epoxidize propylene, typically in the presence of a transition metal catalyst, including titanium, vanadium, molybdenum, or other heavy metal compounds or complexes. Along with the olefin oxide produced, this process disadvantageously produces equimolar amounts of a coproduct, for example an alcohol, such as t-butanol, or an acid, such as acetic acid, whose value must be captured in the market place. (See *Industrial Organic Chemistry*, ibid., pp. 265–269.)

It is known to oxidize olefins directly with oxygen in the presence of a metal oxide, such as a transition metal oxide or a lanthanide rare earth metal oxide, supported on a zeolite carrier. Representative references include U.S. Pat. No. 3,641,066, U.S. Pat. No. 3,957,690, and U.S. Pat. No. 3,963,645. Disadvantageously, these catalysts exhibit low activities and low selectivities to the olefin oxide. Large quantities of partial combustion products, such as acetic acid, and complete combustion products, such as carbon dioxide, are produced.

It is also known to oxidize ethylene directly with oxygen in the presence of a supported silver catalyst containing a transition metal oxide and/or a lanthanide rare earth metal oxide. Zeolites are disclosed as suitable supports. Representative art includes U.S. Pat. No. 5,447,897. While this process may be suitable for producing ethylene oxide selectively, the process fails to produce propylene oxide or higher alkylene oxides in high selectivity.

It is known further to oxidize olefins, including propylene, directly with oxygen in the presence of hydrogen and a catalyst to the corresponding olefin oxide. One catalyst disclosed for this process is a titanosilicate or vanadosilicate containing a platinum group metal or a lanthanide metal. Representative art includes WO-A 96/02323 and WO-A 97/25143. This process also fails to produce propylene oxide in high productivity.

The art also discloses a process of oxidizing $C_3$ and higher olefins directly with oxygen to the olefin oxide, the process being conducted in the presence of hydrogen and a catalyst comprising gold, a titanium-containing support, such as a titanosilicate or titanium dioxide or titanium dispersed on silica, and optionally, at least one promoter element, such as a Group 1, Group 2, a lanthanide, or actinide element. Representative art includes WO-A 98/00413, WO-A 98/00414, and WO-A 98/00415.

In view of the above, a need continues to exist for an efficient direct route to olefin oxides, particularly propylene oxide and higher olefin oxides, from the reaction of oxygen with $C_2$ and higher olefins. The discovery of such a process which simultaneously achieves high selectivity to the olefin oxide at an economically advantageous conversion of the olefin would represent a significant achievement over the prior art. For commercial viability such a process would also require that the catalyst be easily regenerated.

This invention is a novel process of preparing an olefin oxide directly from an olefin and oxygen. The process comprises contacting an olefin with oxygen in the presence of a reducing agent and a catalyst under process conditions sufficient to produce the corresponding olefin oxide. The catalyst employed in the unique process of this invention comprises a metal component dispersed on a metal ion-exchanged metallosilicate.

The novel process of this invention is useful for producing an olefin oxide directly from an olefin and oxygen and a reducing agent. Unexpectedly, the process of this invention produces the olefin oxide in a high selectivity. Partial and complete combustion products, such as acetic acid and carbon dioxide, which are found in large amounts in many prior art processes, are produced in lesser amounts in the process of this invention. Significantly, the process of this invention can be operated at a high temperature, specifically greater than 120° C., while maintaining a high selectivity to olefin oxide. Operation at higher temperatures advantageously provides steam credits from the heat produced. Accordingly, the process of this invention can be integrated into a total plant design wherein the heat derived from the steam is used to drive additional processes, for example, the separation of the olefin oxide from water. Most advantageously, the catalyst can be prepared inexpensively and regenerated easily. Accordingly, the process of this invention is highly desirable for oxidizing olefins directly to olefin oxides.

The novel process of this invention comprises contacting an olefin with oxygen in the presence of a reducing agent and an epoxidation catalyst under process conditions sufficient to prepare the corresponding olefin oxide. In one preferred embodiment, a diluent is employed with one or more of the reactants, as described in detail hereinafter. The relative molar quantities of olefin, oxygen, reducing agent, and optional diluent can be any which are sufficient to prepare the desired olefin oxide. The catalyst, which is described in detail hereinafter, comprises a metal component dispersed on a metal ion-exchanged metallosilicate. In a preferred embodiment of this invention, the olefin employed is a $C_{2-12}$ olefin, and it is converted to the corresponding $C_{2-12}$ olefin oxide. In a more preferred embodiment, the olefin is a $C_{3-8}$ olefin, and it is converted to the corresponding $C_{3-8}$ olefin oxide. In a most preferred embodiment, the olefin is propylene, and the olefin oxide is propylene oxide.

Any olefin can be employed in the process of this invention. Monoolefins are preferred, but compounds containing two or more olefins, such as dienes, can also be employed. The olefin can be a simple hydrocarbon containing only carbon and hydrogen atoms. Alternatively, the olefin can be substituted at any of the carbon atoms with an inert substituent. The term "inert", as used herein, requires the substituent to be substantially non-reactive in the process of this invention. Suitable inert substituents include, but are not limited to, halide, ether, ester, alcohol, and aromatic moieties, preferably, chloro, $C_{1-12}$ ether, ester, and alcohol moieties, and $C_{6-12}$ aromatic moieties. Non-limiting examples of olefins which are suitable for the process of this invention include ethylene, propylene, 1-butene, 2-butene, 2-methylpropene, 1-pentene, 2-pentene, 2-methyl-1-butene, 2-methyl-2-butene, 1-hexene, 2-hexene, 3-hexene, and analogously, the various isomers of methylpentene, ethylbutene, heptene, methylhexene, ethylpentene, propylbutene, the octenes, including preferably 1-octene, and other higher analogues of these; as well as cyclic olefins, such as cyclohexene and cyclooctene. Additional examples of suitable olefins include butadiene, cyclopentadiene, dicyclopentadiene, styrene, α-methylstyrene, divinylbenzene, allyl chloride, allyl alcohol, allyl ether, allyl ethyl ether, allyl butyrate, allyl acetate, allyl benzene, allyl phenyl ether, ally propyl ether, and allyl anisole. Preferably, the olefin is an unsubstituted or substituted $C_{2-12}$ olefin, more preferably, an unsubstituted or substituted $C_{3-8}$ olefin. Most preferably, the olefin is propylene. Many of the aforementioned olefins are available commercially; others can be prepared by chemical processes known to those skilled in the art.

The quantity of olefin employed in the process can vary over a wide range provided that the corresponding olefin oxide is produced. Generally, the quantity of olefin employed depends upon the specific process features, including for example, the design of the reactor, the specific olefin, and economic and safety considerations. Those skilled in the art can determine a suitable range of olefin concentrations for the specific process features desired. Generally, on a molar basis an excess of olefin is used relative to the oxygen, because this condition enhances the productivity to olefin oxide. Based on the process conditions disclosed herein, typically, the quantity of olefin is greater than 1, preferably, greater than 10, and more preferably, greater than 20 mole percent, based on the total moles of olefin, oxygen, reducing agent, and optional diluent. Typically, the quantity of olefin is less than 99, preferably, less than 85, and more preferably, less than 70 mole percent, based on the total moles of olefin, oxygen, reducing agent, and optional diluent.

Oxygen is also required for the process of this invention. Any source of oxygen is acceptable, including air and essentially pure molecular oxygen. Other sources of oxygen may be suitable, including ozone, and nitrogen oxides, such as nitrous oxide. Molecular oxygen is preferred. The quantity of oxygen employed can vary over a wide range provided that the quantity is sufficient for producing the desired olefin oxide. Typically, the quantity of oxygen is greater than 0.01, more preferably, greater than 1, and most preferably greater than 5 mole percent, based on the total moles of olefin, reducing agent, oxygen, and optional diluent. Preferably, the quantity of oxygen is less than 50, more preferably, less than 35, and most preferably less than 20 mole percent, based on the total moles of olefin, reducing agent, oxygen, and optional diluent.

A reducing agent is also required for the process of this invention. In the absence of a reducing agent, the activity of the catalyst is significantly decreased. Any reducing agent can be employed so long as the desired olefin oxide is produced. Non-limiting examples of suitable reducing agents include hydrogen, carbon monoxide, water, alcohols, and saturated hydrocarbons, such as propane. Preferably, the reducing agent is hydrogen. Any source of hydrogen can be used in the process of this invention, including for example, molecular hydrogen obtained from the dehydrogenation of hydrocarbons and alcohols. In an alternative embodiment of this invention, the hydrogen may be generated in situ in the olefin oxidation process, for example, by dehydrogenating alkanes, such as propane or isobutane, or alcohols, such as isobutanol. Alternatively, hydrogen may be used to generate a catalyst-hydride complex or a catalyst-hydrogen complex which can provide the necessary hydrogen to the process.

Any quantity of reducing agent can be employed in the process provided that the amount is sufficient to produce the olefin oxide. Suitable quantities of reducing agent are typically greater than 0.01, preferably, greater than 0.1, and more preferably, greater than 3 mole percent, based on the total moles of olefin, reducing agent, oxygen, and optional diluent. Suitable quantities of reducing agent are typically less than 50, preferably, less than 30, and more preferably, less than 20 mole percent, based on the total moles of olefin, reducing agent, oxygen, and optional diluent.

In addition to the above reagents, it may be desirable to employ a diluent with the reactants, although the use thereof is optional. Since the process of this invention is exothermic, a diluent beneficially provides a means of removing and dissipating the heat produced. In addition, the diluent provides an expanded concentration regime in which the reactants are non-flammable. The diluent can be any gas or liquid which does not inhibit the process of this invention. The specific diluent chosen will depend upon the manner in which the process is conducted. For example, if the process is conducted in a gas phase, then suitable gaseous diluents include, but are not limited to, helium, nitrogen, argon, methane, carbon dioxide, steam, and mixtures thereof. Most of these gases are essentially inert with respect to the process of this invention. Carbon dioxide and steam may not necessarily be inert, but may have a beneficial promoting effect. If the process is conducted in a liquid phase, then the diluent can be any oxidation stable and thermally stable liquid. Examples of suitable liquid diluents include aliphatic alcohols, preferably $C_{1-10}$ aliphatic alcohols, such as methanol and t-butanol; chlorinated aliphatic alcohols, preferably $C_{1-10}$ chlorinated alkanols, such as chloropropanol; chlorinated aromatics, preferably chlorinated benzenes, such as chlorobenzene and dichlorobenzene; as well as liquid polyethers, polyesters, and polyalcohols.

If used, the amount of diluent is typically greater than 0, preferably greater than 0.1, and more preferably, greater than 15 mole percent, based on the total moles of olefin, oxygen, reducing agent, and diluent. The amount of diluent is typically less than 90, preferably, less than 80, and more preferably, less than 70 mole percent, based on the total moles of olefin, oxygen, reducing agent, and diluent.

The aforementioned concentrations of olefin, oxygen, reducing agent, and diluent are suitably based on the reactor designs and process parameters disclosed herein. Those skilled in the art will recognize that concentrations other than the aforementioned ones may be suitably employed in other various engineering realizations of the process.

The unique catalyst which is beneficially employed in the process of this invention comprises a metal component dispersed on a metal ion-exchanged metallosilicate. The metal component can be any elemental metal or metal compound which, as part of the catalyst, is capable of catalyzing the formation of olefin oxide in the process of this invention. Representative examples of suitable metal compounds include metal oxides, organometallic complexes, metal nitrides, metal carbides, metal hydroxides, and metal mixed oxynitrides, oxycarbides, and oxyhydroxides. The metal itself can be present in a metallic state, ionic state, or as a mixed oxidation state cluster (for example, a cluster of "n" metal atoms with an overall +1 charge). The metal component can be a stoichiometric or non-stoichiometric composition. The metal component can be present as clusters, as an amorphous phase, as a quasi-crystalline phase, or as one or more crystalline phases, or combination of aforementioned phases.

Metals which are suitably dispersed as the metal component include the metals of Groups 3 through 14 of the Periodic Table of the Elements, as well as the rare earth lanthanides and actinides, as referenced in the *CRC Handbook of Chemistry and Physics*, 75$^{th}$ edition, CRC Press, Inc., London, 1994–1995. Preferably, the metal of the metal component is selected from titanium, zirconium, vanadium, niobium, tantalum, chromium, molybdenum, tungsten, manganese, rhenium, iron, ruthenium, osmium, cobalt, rhodium, iridium, nickel, palladium, platinum, copper, silver, gold, thallium, tin, bismuth, the rare earth lanthanides, and combinations thereof. More preferably, the metal of the metal component is selected from titanium, zirconium, vanadium, niobium, tantalum, chromium, molybdenum, tungsten, manganese, rhenium, copper, silver, gold, thallium, tin, bismuth, and the rare earth lanthanides.

Optionally, a promoter metal can be dispersed on the metallosilicate in combination with the metal component. The promoter metal is beneficially selected from the Group 1 (alkali) and Group 2 (alkaline earth) elements of the Periodic Table. The promoter metal can likewise be present in a metallic state, ionic state, or ionic cluster, and can also be provided in the form of a promoter metal compound, representative examples of which include Group 1 and Group 2 oxides, hydroxides, nitrides, and mixtures thereof.

The metallosilicate is suitably any metallosilicate possessing cationic sites which are ion-exchangeable. The metallosilicate can be amorphous or crystalline. Preferably, the metallosilicate is porous which means that a series of pores, or channels, and/or cages are present within the framework structure. The pores may be random or regular, and they may be one, two, or three dimensional. Preferably, the pores are micropores or mesopores, or some combination thereof. For the purposes of this invention, a micropore has a diameter (or critical dimension in the case of a non-circular perpendicular cross section) ranging from 4 Å to 20 Å; whereas a mesopore has a diameter or critical dimension ranging from greater than 20 Å to 200 Å.

The pore diameter (or critical dimension), pore size distribution, and surface area of a porous metallosilicate can be obtained from the measurement of adsorption isotherms and pore volume. Typically, the measurements are made on the metallosilicate in powder form using as an adsorbate nitrogen at 77 K or argon at 88 K and using any suitable adsorption analyzer, such as a Micromeritics ASAP 2000 instrument. Measurement of micropore volume is derived from the adsorption volume of pores having a diameter in the range from 4 Å to 20 Å. Likewise, measurement of mesopore volume is derived from the adsorption volume of pores having a diameter in the range from greater than 20 Å to 200 Å. From the shape of the adsorption isotherm, a qualitative identification of the type of porosity, for example, microporous or macroporous, can be made. Additionally, increased porosity can be correlated with increased surface area. Pore diameter (or critical dimension) can be calculated from the data using equations described by Charles N. Satterfield in *Heterogeneous Catalysis in Practice*, McGraw-Hill Book Company, New York, 1980, pp. 106–114.

Typically, the metallosilicate is selected from borosilicates, aluminosilicates, gallosilicates, titanosilicates, and vanadosilicates. Preferably, the metallosilicate is an aluminosilicate, more preferably, a porous aluminosilicate selected from faujasites, such as zeolites X and Y, mordenite, beta, ZSM-3, ZSM-5, ZSM-11, ZSM-12, ZSM-18, ZSM-20, ferrierite, gmelinite, L, omega, offretite, NU-87, MCM-22, and mesoporous silicates, such as MCM-41 and MCM-56. The structures, properties, and syntheses of the aforementioned aluminosilicates are described by R. Szostak, in *Handbook of Molecular Sieves: Structure, Synthesis, Properties*, Chapman & Hall, New York, N.Y., 1992, as well as in other references available to those skilled in the art.

In the process of this invention, the cationic sites of the metallosilicate are required to be ion-exchanged with metal ions. Any metal ion or combination of metal ions can be ion-exchanged into the metallosilicate provided that the resulting ion-exchanged material is capable of producing an olefin oxide in the process of this invention. Suitable, non-limiting examples of metal ions which can be ion-exchanged into the metallosilicate include those of Group 1 (alkali) and Group 2 (alkaline earth) elements, as well as the transition elements of Groups 3–11, the rare earth lanthanides, the actinides, thallium, tin, and lead. Preferably, the Group 11 elements are selected from silver and gold.

Many metallosilicates can be synthesized or purchased in an alkali form, for example the sodium form, and used in the process of this invention as obtained. Alternatively, the alkali form of the metallosilicate can be ion-exchanged with other desirable metal ion(s). The acid and ammonium forms of metallosilicates, which are available commercially or readily synthesized, can also be ion-exchanged with the desired metal ion(s). Ion-exchange is well known in the art and generally comprises slurrying the material to be ion-exchanged with a solution containing a soluble compound of the desired metal ion or ions. Generally, any metal compound, salt, or complex having sufficient solubility in a suitable solvent can be employed. Non-limiting examples of suitable metal compounds include the metal halides, preferably the chlorides, the metal hydroxides, nitrates, sulfates, bicarbonates, alkoxides, and carboxylates, preferably the acetates and lactates. The solvent can be any liquid which is thermally stable under the slurrying conditions and inert with respect to the metallosilicate and the metal ion compound. Water and common organic solvents, for example alcohols, esters, ethers, ketones, aromatic hydrocarbons, and halogenated aromatic hydrocarbons, are typically suitably employed. The concentration of the metal compound in the solution generally ranges from 0.01 M to 10 M, preferably, from 0.1 M to 8 M, and more preferably, from 0.5 M to 5 M. The metallosilicate is generally slurried with the solution at a temperature between ambient, taken as 22° C., and 120° C. for a time ranging from 30 minutes to 24 hours. Thereafter, the metallosilicate is filtered and dried at a temperature ranging from 22° C. to 170° C.

The catalyst of this invention comprising a metal component dispersed on a metal ion-exchanged metallosilicate can be prepared by any suitable method known to those skilled in the art including solution preparations, gas phase preparations, and solid/solid phase preparations. A preferred gas phase method involves contacting the metal ion-exchanged metallosilicate with vapors of a metal compound, such as a metal oxide or a metal oxide precursor compound, so as to deposit the metal compound onto the surface and within any pores of the metallosilicate. Preferably, any metal oxide or metal oxide precursor compound which is readily volatilized is beneficially employed. Suitable precursor compounds include metal carbonyl complexes, metal cyclopentadiene and dicylcopentadiene complexes, methyl metal complexes, and organometallic halides, preferably, the chlorides. Preferably, the metal oxide precursor compound is a metal carbonyl, such as, tungsten carbonyl, rhenium carbonyl, molybdenum carbonyl, or chromium carbonyl.

Any method can be employed for contacting the metal ion-exchanged metallosilicate with vapors of the metal compound. Typically, the desired amount of metal oxide or its precursor compound is heated to a temperature sufficient to obtain a vapor pressure of the oxide or precursor compound. Generally, the temperature is maintained below the temperature of decomposition of the metal oxide or its precursor compound. The metallosilicate can be held at ambient temperature, or alternatively heated to the same temperature or a temperature which is different from the temperature of the metal oxide or metal oxide precursor compound. The deposition time is generally sufficient to volatilize the desired amount of metal oxide or metal oxide precursor compound. Preferably, the deposition time ranges from 1 minute to 24 hours. If a metal oxide is dispersed directly from the vapor state onto the metallosilicate, a subsequent calcination step is not necessary, and the resulting metal oxide loaded metallosilicate can be used as the catalyst without further treatment. If a metal oxide precursor compound is dispersed onto the metallosilicate, then if desired, the precursor-loaded metallosilicate may be calcined under oxygen or air at a temperature and for a time sufficient to convert the precursor compound at least in part to its oxide. Preferably, the calcination is conducted at a temperature between 200° C. and 800° C. for a time ranging from 30 minutes to 24 hours. Alternatively, the precursor-loaded metallosilicate may be used without calcination. In other instances, it may be desirable to reduce the metal compound(s) which are dispersed on the metallosilicate to a metallic state. For example, if a silver or gold compound is dispersed on the metal ion-exchanged metallosilicate, then reduction by standard techniques, for example, heating under a reducing agent, such as hydrogen or ammonia, at a temperature between 30° C. and 500° C., may be employed so as to produce elemental silver or gold. Promoter metals can be deposited in vapor phase preparations in the same manner as the metal component.

In an alternative preparation, the catalyst can be prepared by a solid/solid phase preparation. In this preparative method, the metal component or its precursor compound and any optional promoter metal compounds or promoter metal precursor compounds are mixed in the solid phase with the metal ion-exchanged metallosilicate. The solid mixture is then calcined under an oxygen-containing gas at temperature between 200° C. and 800° C. for a time ranging from 30 minutes to 24 hours. Optionally, the solid material may be reduced by any standard reducing technique, including the one described hereinbefore.

In yet another preparative embodiment, the catalyst employed in the process of this invention can be prepared by solution phase methods, such as precipitation deposition or impregnation. These methods are well known and simply require that the metal component or its precursor compound, and any promoter metal compounds or promoter metal precursor compounds, be solubilized in a suitable solvent from which the metals and/or promoter elements are deposited or precipitated onto the metal ion-exchanged metallosilicate. Afterwards, the metallosilicate can be calcined and/or reduced as described hereinbefore.

The loading of the metal component onto the metallosilicate can vary so long as the olefin oxide is produced in the process of this invention. Typically, the loading of the metal component is greater than 0.001 weight percent, preferably, greater than 0.01 weight percent, based on the total weight of catalyst. Generally, the loading of the metal component is less than 50 weight percent. Preferably, the loading of the metal component is no greater than that necessary to fill the void space of the metallosilicate. One skilled in the art will know how to determine the quantity of metal component which fills the void space of the metallosilicate.

Likewise, the loading of the promoter metal(s) onto the metallosilicate can be any which gives rise to the desired olefin oxide in the process of this invention. Generally, the loading of the promoter metal(s) is greater than 0.001 weight percent, preferably, greater than 0.01 weight percent, based on the total weight of catalyst. Generally, the loading of the promoter metal(s) is less than 50 weight percent, and preferably, no greater than that required to fill the void space of the metallosilicate after the desired amount of metal component has been loaded.

The catalyst composition comprising a metal component and, optionally, one or more promoter elements dispersed on a metal ion-exchanged metallosilicate embraces within its scope any combination of metal components, promoter elements, and metal ion-exchanged metallosilicates described hereinabove. Preferably, however, the catalyst composition does not include compositions consisting of a metal component selected from one or more Group VIII elements, lanthanide elements, rhenium, silver, and gold dispersed on titanosilicate or vanadosilicate. In another preferred embodiment, the catalyst composition does not include compositions consisting of a metal component selected from silver and gold with at least one promoter element selected from Group 1, Group 2, and the rare earth lanthanide and actinide elements, dispersed on titanosilicate.

Optionally, the catalyst of this invention can be extruded with, bound to, or supported on a second support, such as silica, alumina, an aluminosilicate, magnesia, titania, carbon, or mixtures thereof. The second support may function to improve the physical properties of the catalyst, such as, the strength or attrition resistance, or to bind the catalyst particles together. Generally, the quantity of second support ranges from 0 to 95 weight percent, based on the combined weight of the catalyst and second support.

The process of this invention can be conducted in a reactor of any conventional design suitable for gas or liquid phase processes. These designs broadly include batch, fixed-bed, transport bed, fluidized bed, moving bed, trickle bed, and shell and tube reactors, as well as continuous and intermittent flow and swing reactor designs. Alternatively, the process may be conducted in two steps wherein the catalyst is first contacted with oxygen and thereafter the oxygenated catalyst is contacted with a mixture of olefin and reducing agent. If the process is conducted in the gas phase, then preferably, the reactor is designed with heat transfer features for the removal of the heat produced. Preferred reactors designed for these purposes include fixed-bed, shell and tube, fluidized bed, and moving bed reactors, as well as swing reactors constructed from a plurality of catalyst beds connected in parallel and used in an alternating fashion. If the process is conducted in the liquid phase, then preferred reactors include fixed bed and trickle bed reactors.

The process conditions for the direct oxidation described herein can vary considerably over a nonflammable and flammable regime. It is beneficial, however, to recognize the conditions which distinguish between nonflammable and flammable mixtures of the olefin, reducing agent, and oxygen. Accordingly, a phase diagram can be constructed or consulted which for any given process temperature and pressure shows the flammable and non-flammable range of reactant compositions, including the diluent, if used.

Usually, the process is conducted at a temperature which is greater than ambient, taken as 20° C., preferably, greater than 70° C., more preferably, greater than 120° C. Usually, the process is conducted at a temperature less than 250° C., preferably, less than 225° C., more preferably, less than 200° C. Preferably, the pressure ranges from atmospheric to 400 psig (2758 kPa), more preferably, from 150 psig (1034 kPa) to 250 psig (1724 kPa).

In flow reactors the residence time of the reactants and the molar ratio of reactants to catalyst will be determined by the space velocity. For a gas phase process the gas hourly space velocity (GHSV) of the olefin can vary over a wide range, but typically is greater than 10 ml olefin per ml catalyst per hour ($h^{-1}$), preferably, greater than 100 $h^{-1}$, and more preferably, greater than 1,000 $h^{-1}$. Typically, the GHSV of the olefin is less than 50,000 $h^{-1}$, preferably, less than 35,000 $h^{-1}$, and more preferably, less than 20,000 $h^{-1}$. Likewise, for a liquid phase process the weight hourly space velocity (WHSV) of the olefin component may vary over a wide range, but typically is greater than 0.01 g olefin per g catalyst per hour ($h^{-1}$), preferably, greater than 0.05 $h^{-1}$, and more preferably, greater than 0.1 $h^{-1}$. Typically, the WHSV of the olefin is less than 100 $h^{-1}$, preferably, less than 50 $h^{-1}$, and more preferably, less than 20 $h^{-1}$. The gas and weight hourly space velocities of the oxygen, reducing agent, and diluent components can be determined from the space velocity of the olefin taking into account the relative molar ratios desired.

When an olefin having at least three carbon atoms is contacted with oxygen in the presence of a reducing agent and the catalyst described hereinabove, the corresponding olefin oxide (epoxide) is produced in good productivity. The most preferred olefin oxide produced is propylene oxide.

The conversion of olefin in the process of this invention can vary depending upon the specific process conditions employed, including the specific olefin, temperature, pressure, mole ratios, and form of the catalyst. As used herein, the term "conversion" is defined as the mole percentage of olefin which reacts to form products. Generally, the conversion increases with increasing temperature and pressure and decreases with increasing GHSV. Typically, an olefin conversion of greater than 0.1 mole percent is achieved. Preferably, the olefin conversion is greater than 0.3 percent.

Likewise, the selectivity to olefin oxide can vary depending upon the specific process conditions employed. As used herein, the term "selectivity" is defined as the mole percentage of reacted olefin which forms a particular product, desirably the olefin oxide. Generally, the selectivity to olefin oxide will decrease with increasing temperature and increase with increasing space velocity. The process of this invention produces olefin oxides in unexpectedly high selectivity. A typical selectivity to olefin oxide in this process is greater than 50, preferably, greater than 70, and more preferably, greater than 80 mole percent.

When its activity has decreased to an unacceptably low level, the catalyst of this invention can be easily regenerated. Any catalyst regeneration method generally known to those skilled in the art can be employed provided that the catalyst is reactivated for the oxidation process described herein. One suitable regeneration method comprises heating the deactivated catalyst at a temperature between 150° C. and 500° C. under an atmosphere of a regeneration gas containing oxygen and optionally an inert gas. A preferred regeneration temperature varies between 200° C. and 400° C. The amount of oxygen in the regeneration gas can be any which effectively regenerates the catalyst. Preferably, the oxygen comprises from 2 to 100 mole percent of the regeneration gas. Suitable inert gases are non-reactive and include, for example, nitrogen, helium, and argon. The regeneration cycle time, that is the time during which the catalyst is being regenerated, can range from as little as 2 minutes to as long as several hours, for example, 20 hours at the lower regeneration temperatures. In an alternative embodiment, water may be beneficially added to the regeneration gas in an amount preferably ranging from 0.01 to 100 mole percent.

The invention will be further clarified by a consideration of the following examples, which are intended to be purely exemplary of the use of the invention. Other embodiments of the invention will be apparent to those skilled in the art from a consideration of this specification or practice of the invention as disclosed herein. Unless otherwise noted, all percentages are given on a mole percent basis.

Preparation of Catalysts

The following general procedure was employed to prepare a series of epoxidation catalysts comprising a transition metal oxide dispersed on zeolite NaY or BaY. In examples with NaY, the zeolite was used as purchased from UOP (LZY-52), and no ion-exchange was necessary. In examples with BaY, the BaY was obtained by ion-exchanging the NaY with a barium salt. Specifically, the NaY was slurried with an excess of aqueous solution of barium chloride (0.1 M) at room temperature for 17 h. The slurry was filtered, and the solid obtained was washed with water (4 l) and then dried at 50° C. for 6 h.

The zeolite was placed in a reactor containing a side arm and calcined by heating at 5° C./min to 450° C. and holding at 450° C. for 2 h under oxygen. Then, the reactor was evacuated and cooled to room temperature. A metal carbonyl compound was placed in the side arm of the reactor and heated under vacuum to 150° C. Under these conditions, the metal carbonyl sublimed and its vapors dispersed onto and into the zeolite. The reagents used were as follows: (1) rhenium carbonyl (40 mg) with BaY (1.400 g); (2) tungsten carbonyl (105 mg) with BaY (1.999 g); (3) molybdenum carbonyl (90 mg) with NaY (2.293 g); and (4) chromium carbonyl (78 mg) with NaY (1.683 g). The metal carbonyl-loaded zeolite was then calcined under oxygen at 150° C. and 250 torr (33 kPa) for 1 h yielding the following epoxidation catalysts: (1) rhenium oxide-loaded BaY; (2) tungsten oxide-loaded BaY; (3) molybdenum oxide-loaded NaY; and (4) chromium oxide-loaded NaY.

EXAMPLES 1–4

Epoxidation of Propylene to Propylene Oxide

The catalysts prepared hereinabove were tested in the direct oxidation of propylene with oxygen in the presence of hydrogen to form propylene oxide. The general epoxidation procedure was as follows: A tubular, continuous flow reactor [0.5 inch (1.3 cm)×6 inch (15.0 cm) length] was loaded with catalyst as specified in Table I. A feed comprising 30 percent propylene, 10 percent oxygen, 10 percent hydrogen, and the balance helium was flowed continuously over the catalyst at a rate of 150 cm³/min (GHSV 4500 h⁻¹) at 150° C. and atmospheric pressure. Propylene, oxygen and helium were used as pure streams; hydrogen was mixed with helium in a 20 H$_2$/80 He (v/v) mixture. The composition of the outlet stream was analyzed by gas chromatography with the results shown in Table I.

TABLE I

Oxidation of Propylene (PP) to Propylene Oxide (PO)[a]

| Ex. | Catalyst (g) | % Selectivity PO | % Conversion PP |
|---|---|---|---|
| 1 | BaY/Re$_2$O$_7$ (0.88 g) | 85 | 0.11 |
| 2 | BaY/WO$_3$ (1.04 g) | 80 | 0.09 |
| 3 | NaY/MoO$_3$ (0.95 g) | 67 | 0.65 |
| 4 | NaY/CrO$_3$ (2.00 g) | 73 | 0.28 |

[a]Feed: 30% propylene, 10% oxygen, 10% hydrogen, 50% helium; Temperature, 150° C.; Pressure, atmospheric; Flow feed, 150 cm³/min (GHSV 4,500 h⁻¹)

It is seen in Table I that a catalyst comprising a transition metal oxide dispersed on a metal ion-exchanged porous aluminosilicate, specifically NaY or BaY, is capable of oxidizing propylene directly with oxygen in the presence of hydrogen to propylene oxide. Propylene conversions vary from 0.09 to 0.65 percent. Selectivity to propylene oxide varies from 67 to 85 percent, the latter for a rhenium oxide-loaded BaY catalyst.

Comparative Experiments 1–4

Examples 1–4 were each repeated as described hereinabove, with the exception that hydrogen was excluded from the process. No propylene oxide was detected in any experiment. Only a trace of carbon dioxide was detected in Comparative Experiments 3 (NaY/MoO$_3$) and 4 (NaY/CrO$_3$). When Examples 1–4 are compared with the corresponding Comparative Experiments 1–4, it is seen that the presence of hydrogen in the process significantly increases catalytic activity and selectivity for propylene oxide.

EXAMPLES 5–8

Oxidation Process Using Regenerated Catalysts

The catalysts of Examples 1–4 were regenerated by heating the used catalysts at 300° C. in a stream comprising 10 percent oxygen in helium. The regenerated catalysts were tested in the oxidation of propylene with oxygen in the presence of hydrogen in the manner set forth in Examples 1–4. Process conditions and results are set forth in Table II.

TABLE II

Oxidation of Propylene (PP) to Propylene Oxide (PO) Using Regenerated Catalysts[a]

| Ex. | Regenerated Catalyst (g) | % Sel PO | % Conv PP |
|---|---|---|---|
| 5 | BaY/Re$_2$O$_7$ (0.88 g) | 93 | 0.15 |
| 6 | BaY/WO$_3$ (1.04 g) | 88 | 0.11 |
| 7 | NaY/MoO$_3$ (0.95 g) | 61 | 0.61 |

TABLE II-continued

Oxidation of Propylene (PP) to Propylene Oxide (PO) Using Regenerated Catalysts[a]

| Ex. | Regenerated Catalyst (g) | % Sel PO | % Conv PP |
|---|---|---|---|
| 8 | NaY/CrO$_3$ (2.00 g) | 75 | 0.54 |

[a]Feed: 30% propylene, 10% oxygen, 10% hydrogen, 50% helium; Temperature, 150° C.; Pressure, atmospheric; Flow feed, 150 cm³/min (GHSV 4,500 h⁻¹)

It is seen in Table II that the regenerated catalysts of Examples 1–4 comprising a transition metal oxide dispersed on a metal ion-exchanged porous aluminosilicate are active in oxidizing propylene directly with oxygen in the presence of hydrogen to propylene oxide. In Examples 5, 6, and 8, the regenerated catalyst is more active and more selective for propylene oxide than the corresponding fresh catalyst.

Comparative Experiments 7–8

Examples 7 and 8 were repeated as described hereinabove, with the exception that hydrogen was excluded from the process. No propylene oxide was detected. Only a trace of carbon dioxide was detected in Comparative Experiment 7 (NaY/MoO$_3$). When Examples 7 and 8 are compared with the corresponding Comparative Experiments 7 and 8, it is seen that the presence of hydrogen in the process significantly increases catalytic activity and selectivity.

EXAMPLE 9

Zeolite Y (UOP, LZY-52, 20 g) was slurried in an aqueous solution of sodium chloride (1 l; 0.1 M). The slurry was stirred for 6 h and filtered. The filtered product was washed until chloride free. The washed product was dried at room temperature, and then calcined in air from room temperature to 480° C. in 8 h and then held at 480° C. for 4 h. The calcined material (10 g) was placed in a flask and stirred with an aqueous solution of silver nitrate (1 l; 0.1 M) for 48 h. The flask was kept away from light. The slurry was filtered, and the filtered product was washed free of chloride and dried in the dark at room temperature. The material was calcined at 480° C. for 2 h. The calcined, dehydrated silver-exchanged Y zeolite (2.306 g) was ground together with rhenium carbonyl (60 mg) in a mortar in a glove box for 5 min. The mixture was calcined under oxygen at 150° C., and then the calcined material was reduced at 150° C. in 600 torr of hydrogen. The catalyst (1.75 g) was tested in the hydro-oxidation of propylene in the manner described in Examples 1–4 with the following results: at 125° C., conversion of propylene, 0.34 percent; selectivity to propylene oxide, 82 percent.

What is claimed is:

1. A process of preparing an olefin oxide comprising contacting an olefin with oxygen in the presence of a reducing agent and an optional diluent, and in the presence of a catalyst comprising a metal component dispersed on a metal ion-exchanged metallosilicate, wherein the contacting occurs under process conditions sufficient to produce the olefin oxide; and wherein the metallosilicate is selected from borosilicates, aluminosilicates, gallosilicates, and vanadosilicates, and with the proviso that when the metallosilicate is a vanadosilicate the catalyst does not consist of a metal component selected from one or more Group VIII elements, lanthanide elements, rhenium, silver, and gold dispersed on the vanadosilicate.

2. The process of claim 1 wherein the olefin is a $C_{2-12}$ olefin.

3. The process of claim 2 wherein the olefin is propylene, butadiene, cyclopentadiene, dicyclopentadiene, cyclohexene, cyclooctene, styrene, α-methylstyrene, divinylbenzene, allyl chloride, allyl alcohol, allyl ether, allyl ethyl ether, allyl butyrate, allyl acetate, allyl benzene, allyl phenyl ether, allyl propyl ether, and allyl anisole.

4. The process of claim 1 wherein the olefin is used in a quantity greater than 1 and less than 99 mole percent, based on the total moles of olefin, oxygen, reducing agent, and optional diluent.

5. The process of claim 1 wherein the oxygen is used in a quantity greater than 0.01 and less than 50 mole percent, based on the total moles of olefin, oxygen, reducing agent, and optional diluent.

6. The process of claim 1 wherein the reducing agent is used in a quantity greater than 0.01 and less than 50 mole percent, based on the total moles of olefin, oxygen, reducing agent, and optional diluent.

7. The process of claim 1 wherein the reducing agent is hydrogen.

8. The process of claim 1 wherein a diluent is used such that when the process is conducted in a vapor phase, the diluent is selected from helium, nitrogen, argon, methane, carbon dioxide, steam, and mixtures thereof; and wherein when the process is conducted in a liquid phase, the diluent is selected from chlorinated benzenes, $C_{1-10}$ aliphatic alcohols, chlorinated $C_{1-10}$ alkanols, liquid polyethers, polyalcohols, and polyesters.

9. The process of claim 1 wherein a diluent is used in a quantity greater than 0 and less than 90 mole percent, based on the total moles of olefin, oxygen, reducing agent, and optional diluent.

10. The process of claim 1 wherein the metal component is selected from the elemental metals and metal compounds of the elements of Groups 3–14, the rare earth lanthanides, and the actinides of the Periodic Table of the Elements, and combinations thereof.

11. The process of claim 1 wherein the metal component is a metal compound selected from metal oxides, metal carbides, metal nitrides, metal hydroxides, metal oxycarbides, metal oxynitrides, and metal oxyhydroxides.

12. The process of claim 11 wherein the metal oxide is tungsten oxide, rhenium oxide, molybdenum oxide, or chromium oxide.

13. The process of claim 1 wherein the metal of the metal component is selected from titanium, zirconium, vanadium, niobium, tantalum, chromium, molybdenum, tungsten, manganese, rhenium, iron, ruthenium, osmium, cobalt, rhodium, iridium, nickel, palladium, platinum, copper, silver, gold, thallium, tin, bismuth, the rare earth lanthanides, and combinations thereof.

14. The process of claim 1 wherein a porous aluminosilicate is employed selected from faujasites, mordenite, beta, ZSM-3, ZSM-5, ZSM-11, ZSM-12, ZSM-18, ZSM-20, ferrierite, gmelinite, L, omega, offretite, NU-87, MCM-22, MCM-41, and MCM-56.

15. The process of claim 14 wherein the faujasite is zeolite Y.

16. The process of claim 1 wherein the metallosilicate is ion-exchanged with one or more metal ions selected from Group 1, Group 2, Groups 3–11, the rare earth lanthanides, the actinide elements, thallium, tin, and lead elements of the Periodic Table.

17. The process of claim 1 wherein additionally one or more promoter elements selected from Group 1 and Group 2 elements and combinations thereof, is dispersed on the metallosilicate.

18. The process of claim 1 wherein the loading of the metal component is greater than 0.001 weight percent, based on the total weight of the catalyst, and no greater than the quantity of metal component required to fill the void space of the metallosilicate.

19. The process of claim 1 wherein the catalyst is bound to a second support.

20. The process of claim 1 wherein the process is conducted at a temperature greater than 20° C. and less than 250° C.

21. The process of claim 1 wherein when the process is conducted in a gaseous phase, the gas hourly space velocity of the olefin is greater than 10 h$^{-1}$ and less than 50,000 h$^{-1}$, or wherein when the process is conducted in a liquid phase, the weight hourly space velocity of the olefin is greater than 0.01 h$^{-1}$ and less than 100 h$^{-1}$.

22. The process of claim 1 wherein the pressure ranges between atmospheric and 400 psig.

23. The process of claim 1 wherein the process is conducted in a reactor selected from batch, fixed bed, transport bed, moving bed, fluidized bed, trickle bed, shell and tube, continuous flow, intermittent flow, and swing reactors.

24. The process of claim 1 wherein the catalyst is regenerated under oxygen at a temperature between 150° C. and 500° C.

25. The process of claim 1 wherein the catalyst is prepared by contacting vapors of a metal oxide or a metal oxide precursor compound with a metal ion-exchanged metallosilicate.

26. The process of claim 25 wherein after contacting the metal ion-exchanged metallosilicate with vapors of a metal oxide or a metal oxide precursor compound, the metallosilicate is calcined under oxygen at a temperature between 200° C. and 800° C.

27. The process of claim 25 wherein the preparation additionally comprises a reduction step.

28. The process of claim 25 wherein the precursor compound is a metal carbonyl complex, a metal cyclopentadiene or metal dicyclopentadiene complex, a methyl metal complex, or an organometallic chloride.

29. The process of claim 28 wherein the metal carbonyl is tungsten carbonyl, molybdenum carbonyl, rhenium carbonyl, or chromium carbonyl.

30. The process of claim 1 wherein the catalyst is prepared by contacting a metal compound with a metal ion-exchanged metallosilicate in the solid phase to yield a solid comprising a metal component dispersed on a metal ion-exchanged metallosilicate, and thereafter, optionally, calcining the solid at a temperature between 200° C. and 800° C., and optionally, reducing the solid at a temperature between 30° C. and 500° C.

* * * * *

UNITED STATES PATENT AND TRADEMARK OFFICE
CERTIFICATE OF CORRECTION

PATENT NO. : 6,362,349 B1
DATED : March 26, 2002
INVENTOR(S) : Alex Kuperman et al.

It is certified that error appears in the above-identified patent and that said Letters Patent is hereby corrected as shown below:

<u>Title page,</u>
ABSTRACT,
Line 1, after the word "olefin" insert therefore -- , such as propylene, --
Line 2, after the word "oxide" insert therefore -- , such as propylene oxide. The process involves contacting the olefin with oxygen under reaction conditions --
Line 3, after the word "and" insert therefore -- , such as hydrogen, and in the presence of --

Signed and Sealed this

Twenty-sixth Day of November, 2002

*Attest:*

JAMES E. ROGAN
*Attesting Officer*   *Director of the United States Patent and Trademark Office*